United States Patent [19]

Chua

[11] Patent Number: 4,967,744
[45] Date of Patent: Nov. 6, 1990

[54] FLEXIBLE BREATHING CIRCUIT

[75] Inventor: James Chua, Riverside, Calif.

[73] Assignee: Airoflex Medical, Inc., Riverside, Calif.

[21] Appl. No.: 266,556

[22] Filed: Nov. 3, 1988

[51] Int. Cl.[5] .................. A61M 16/01; F16L 9/19; F16L 11/08; F16L 11/12

[52] U.S. Cl. .................. 128/204.18; 128/911; 128/912; 128/204.17; 138/113

[58] Field of Search .................. 128/202.27, 204.17, 128/204.18, 911, 912

[56] References Cited

U.S. PATENT DOCUMENTS

| | | | |
|---|---|---|---|
| 2,073,335 | 3/1937 | Connell | 128/204.18 |
| 2,820,651 | 1/1958 | Phillips | 128/204.18 |
| 3,163,707 | 12/1964 | Darling | 174/47 |
| 3,491,754 | 1/1970 | Weese | 128/204.17 |
| 3,670,726 | 6/1972 | Mahon et al. | 128/204.18 |
| 3,824,999 | 7/1974 | King | 128/185 |
| 3,856,051 | 12/1974 | Bain | 128/204.18 |
| 3,858,615 | 1/1975 | Weigl | 138/121 |
| 3,865,106 | 2/1975 | Palush | 128/145.8 |
| 3,978,854 | 9/1976 | Mills, Jr. | 128/912 |
| 4,007,737 | 2/1977 | Paluch | 128/911 |
| 4,232,667 | 11/1980 | Chalon et al. | 128/204.17 |
| 4,265,235 | 5/1981 | Fukunaga | 128/205.12 |
| 4,367,769 | 1/1983 | Bain | 138/114 |
| 4,463,755 | 8/1984 | Suzuki | 128/204.18 |
| 4,621,634 | 11/1986 | Nowacki et al. | 128/204.18 |
| 4,637,384 | 1/1987 | Schroeder | 128/204.18 |
| 4,682,010 | 7/1987 | Drapeau et al. | 128/204.17 |
| 4,686,354 | 8/1987 | Makin | 128/204.17 |
| 4,737,153 | 4/1988 | Shimamura | 604/282 |
| 4,767,409 | 8/1988 | Brooks | 604/171 |
| 4,808,767 | 2/1989 | Colbachini | 128/201.27 |
| 4,840,172 | 6/1989 | Augustine | 128/207 |

FOREIGN PATENT DOCUMENTS 2154145 9/1985 United Kingdom ........... 128/911
2173274A 10/1986 United Kingdom .

Primary Examiner—Edgar S. Burr
Assistant Examiner—Kimberly L. Asher
Attorney, Agent, or Firm—Lyon & Lyon

[57] ABSTRACT

A breathing circuit for providing conduit from a breathing apparatus or anaesthetic device to a patient, the breathing circuit being generally coaxial and including a first flexible tube and a second flexible tube inside the first flexible tube. The first flexible tube has a smooth inner surface and a reinforcing cord or ribbing along its length and integral around its outer surface. The first flexible tube has a relatively thin wall with the cord, which is preferably in a spiral, providing structural strength or stiffness while retaining flexibility.

16 Claims, 2 Drawing Sheets

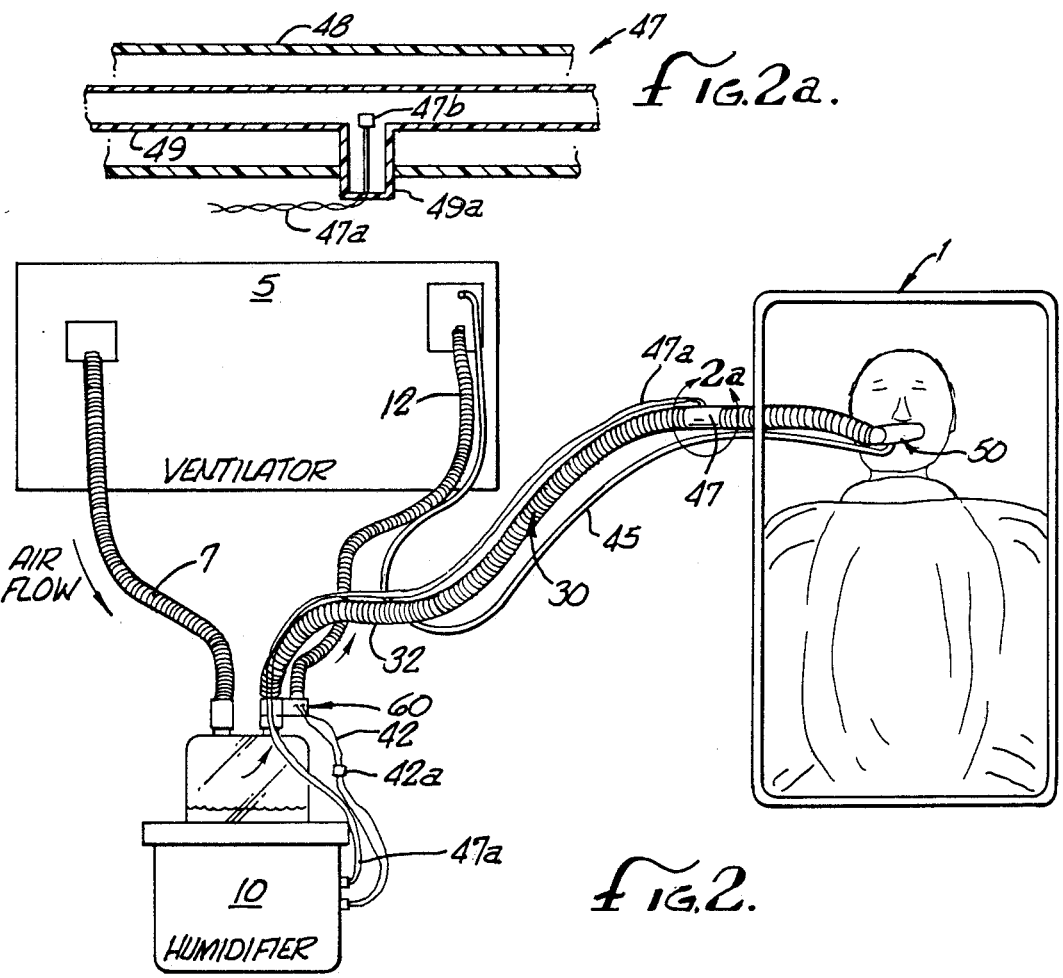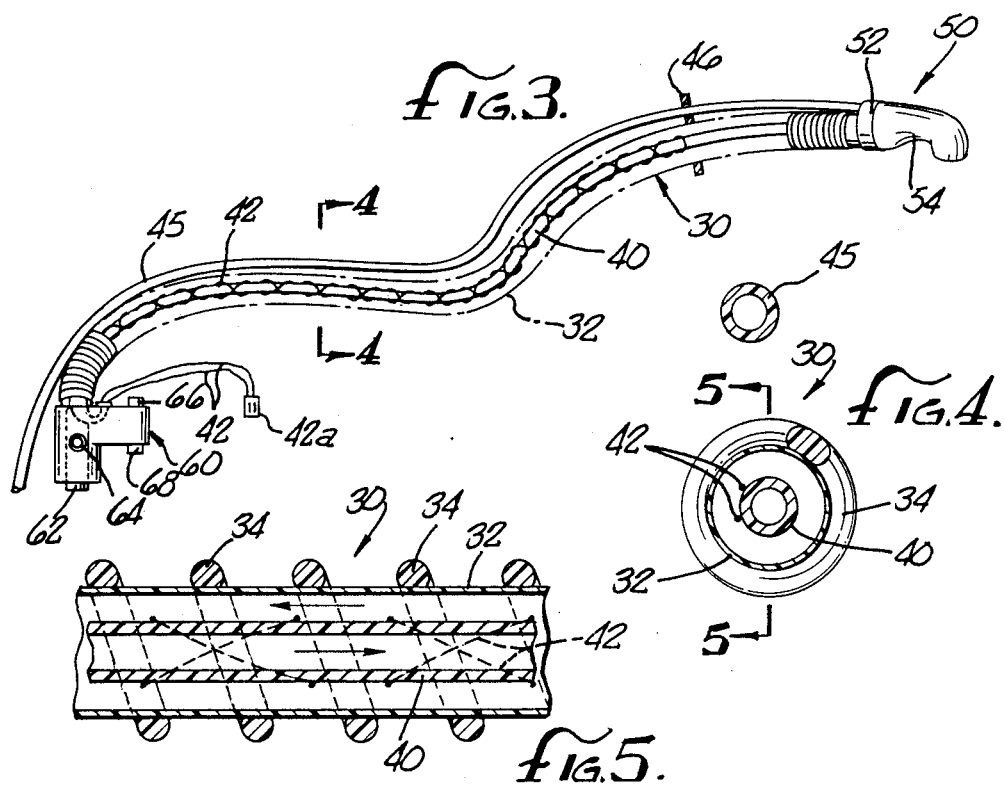

FLEXIBLE BREATHING CIRCUIT

BACKGROUND OF INVENTION

The field of the present invention relates to breathing circuits or more particularly to a flexible tubular device to be connected to a breathing apparatus or anaesthetic system on one end with the other end applied to nasal or oral regions of a patient. The present invention is particularly applicable for infants and premature babies.

There are existing flexible tube devices which include a coaxial arrangement with a first tubular member on the outside and a second smaller tubular member running coaxially inside the first tubular member. Another existing device is the parallel line design illustrated in FIG. 1b having corrugated inspiratory tubular member 240 separate from corrugated expiratory tubular member 230. A device of the coaxial design is disclosed in Bain U.S. Pat. No. 3,856,051. The Bain device is illustrated in FIG. 1a. Referring to FIG. 1a, the Bain device 100 is comprised of a corrugated outer tubular member 110 and an inner tubular member 120 running inside the corrugated member 110. Typically the inner tubular member 120 is the inspiratory channel and the outer corrugated tubular member 110 (or more specifically the volume between the inner and outer tubular members) is the expiratory channel.

This corrugated tubular device has several deficiencies. In particular, the corrugated tubular member 110 must be flexible enough to allow convenient movement and adjustment of the tube 100 while simultaneously providing sufficient stiffness and structural strength to withstand damage from use, avoid collapse, and provide structure for attachment of additional tubings which may be required for a particular application. It is also desirable that both the expiratory and inspiratory channels exhibit low air flow resistance.

SUMMARY OF THE INVENTION

The present invention is directed to a breathing circuit for providing a conduit from a breathing apparatus or anaesthetic device to a patient. To this end, a coaxial breathing circuit includes a first flexible tube and a second flexible tube inside the first flexible tube and generally coaxial therewith. The first flexible tube has a smooth inner surface and a reinforcing cord or ribbing along its length and integral around its outer surface. The first flexible tube has a relatively thin wall with the cord, which is preferably in a spiral, providing structural strength or stiffness while retaining flexibility. The breathing circuit is connectable to a swiveling patient connector at one and to a multiport manifold at its other end.

BRIEF DESCRIPTION OF THE DRAWINGS

FIG. 2 diagrammatically illustrates a breathing circuit attached to a breathing apparatus and running to a patient;

FIG. 2a diagrammatically illustrates in cross section the connection passage of the breathing circuit of FIG. 2;

FIG. 3 is illustrates the breathing circuit according to the present invention in partial cutaway showing an internal coaxial tube;

FIG. 4 is a cross sectional view of the coaxial tube breathing circuit of FIG. 3 taken along the line 4—4; and FIG. 5 is a lengthwise cross sectional view of the breathing circuit of FIG. 4 taken along the line 5—5;

DETAILED DESCRIPTION OF THE PREFERRED EMBODIMENT

Figure 1A:
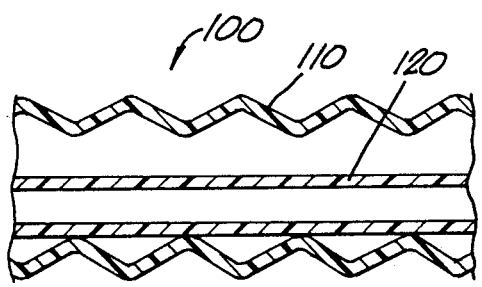
FIG. 1a is a cross section of a prior art coaxial flexible tubing.

The preferred embodiment will now be described with reference to the drawings. To facilitate the description, any element represented by a numeral in one figure will be represented by the same numeral in any other figure.

FIG. 2 diagrammatically illustrates a coaxial tube 30 connecting a ventilator 5 and humidifier 10 to a patient in the incubator 1. The coaxial tube 30 has an inspiratory line 40 inside an outer tubing 32. The coaxial tube 30 therefore has two passageways: (1) an inspiratory or inhalation passageway provided by the inspiratory supply line 40 and (2) an exhalation or expiratory passageway provided by the volume between the inspiratory supply line 40 and the outer tubing 32.

Air flows from the ventilator 5 through the inlet line 7 and to the chamber in the humidifier 10. Also referring to FIG. 3, humidified air enters the inspiratory supply line 40, which provides the inhalation passageway of the coaxial tube 30 to the patient in an incubator 1. As the patient exhales, the expiratory line 32 providing the exhalation passageway carries the exhaled air back to a breathing connector 60 and the gases return to the ventilator 5 through a return line 12.

Additional lines and features are provided for monitoring and controlling temperature and pressure. A proximal airway pressure line 45 is connected between the patient connector 50 and the ventilator 5 so the pressure at the patient may be monitored and adjusted if necessary. Temperature of the traveling gases may be monitored at a remote temperature port 47 which is connected by electrical temperature monitoring lines 47a running back to a temperature controller at the humidifier 10.

Details of a remote temperature port 47 are shown in FIG. 2a. The temperature port 47 is a coaxial connector joint which is interposed between lengths of the coaxial tube 30. The outer wall 48 provides connection between consecutive expiratory lines 32 and the inner passage 49 provides connection between consecutive inspiratory lines 40. A connection passage 49a provides an isolated path through the expiratory passageway to the inspiratory passage so a temperature probe 47b may be inserted to monitor the temperature in the inspiratory line 40.

Referring specifically to FIGS. 3-5, to control the temperature of the inlet and outlet gases, a heating wire 42 may be added and conveniently wrapped around the inspiratory supply line 40. At the end of the heating wire 42 is a heating wire connector 42a which may be connected to a thermostatic controller (not shown) which may be included within the humidifier 10. Additionally, the return line 12 may also contain a heating wire (not shown).

The coaxial tube 30 has a connection means on each end thereof. On the patient end, the connection means includes a swivel patient connector 50. The swivel patient connector 50 is comprised of an end piece 54 and a connector ring 52 to which the inner tube 40 and the outer tubes 32 and 45 are attached. The end piece 54 is rotatably connected to the ring 52 so that by a swivel action, the orientation of the swivel patient connector 50 may be adjusted to accommodate varying positions of the patient without requiring twisting of the coaxial tube 30. Though not shown, the end piece 54 may be connected to a respiratory mouthpiece or the like.

On the breathing apparatus end of the coaxial tube 30 is an air supply connector 60. The air supply connector 60 is a compact adapter which includes outlets for the air passages and for the various monitoring lines. The inspiratory supply line 40 is connected through a supply passage 62 to the humidifier 10. The supply connector 60 may have a standard 22 mm fitting common to many neonatal ventilators and humidification systems. A temperature monitor port 64 is also connected to the inspiratory supply line 40 allowing temperature measurement of the air leaving the humidifier 10. The expiratory tube 32 is connected to an exit connector 66 to which the air line 12 running back to the ventilator is attached. An additional expiratory connector is also provided for alternate attachment to another line such as air line 12 depending upon particular application. The heating wires 42 exit through the side wall of the air supply connector 60 and the wires are sealed in place to prevent escape of air at the point of exit. The heating wire connector 42a may then be connected to a thermostatic control means (not shown).

FIG. 4 shows a cross sectional view of a coaxial tube 30 and the proximal airway pressure line 45. As can be seen from the figure, the expiratory tube 32 has a relatively thin wall as compared to the tubing of the inspiratory supply line 40 and the proximal airway pressure line 45. Both the inner and outer surfaces of the inspiratory supply line 40 are smooth which help minimize both inspiratory and expiratory flow resistance. The coaxial tube 30 of the illustrated preferred embodiment provides a superior breathing circuit for infants and premature babies. As such, the coaxial tube is fairly small in size and bulk. The expiratory tube 32 has an inner diameter of about 15 millimeters (mm) with a wall thickness of about ½ mm. The inspiratory tube 40 is a thicker tubing having an inner diameter of about 5 mm and a wall thickness of about 1 mm. These dimensions are intended to be illustrative.

As shown in FIGS. 4 and 5, the expiratory tube 32 is a relatively thin wall and highly flexible tubing having an outer support structure comprised of spiral cord or ribbing 34 running the length of the tube 32 along its exterior. The cord 34 provides structural strength and stiffness to the coaxial tube 30 while maintaining flexibility. The structural strength and stiffness provided gives protection from crushing applied by external forces, helps avoid pressure collapse, and reduces compliance which is the tendency of a tubing to expand or contract upon changes of pressure. Though the cord 34 is preferably spiral or helical around the expiratory tube 32, other shapes are feasible though some may not be as effective.

One alternative design would include a plurality of stiffening rings spaced about the exterior of expiratory tube 32. The stiffening rings may be arranged in a generally concentric fashion to the outside of the expiratory tube 32 in a manner similar to the spiral cord 34, the rings being spaced consecutively along the length of the expiratory tube. Preferably this alternative would include connections between adjacent rings to maintain low compliance.

The present invention is particularly applicable for infants and premature babies. An infant's breathing rate is very high so the breathing cycle or period from inhalation phase to the exhalation phase is very short. A premature baby's lungs are small and stiff requiring an even higher breathing rate i.e., a shorter, faster cycle. Consequently a high flow rate is required during the inspiratory or inhalation phase to transfer the desired volume of air to the infant's lungs within this short cycle. The higher the peak pressure, the higher the flow rate required to achieve this peak pressure. As the flow rate increases so does expiratory resistance. During the exhalation phase, the patient must exhale air out the expiratory tubing 32. It is desired to minimize back pressure within the expiratory tube so the patient does not have to overcome such pressure upon exhalation. It is therefore desirable to minimize sources of both expiratory back pressure and expiratory resistance.

Figure 1B:
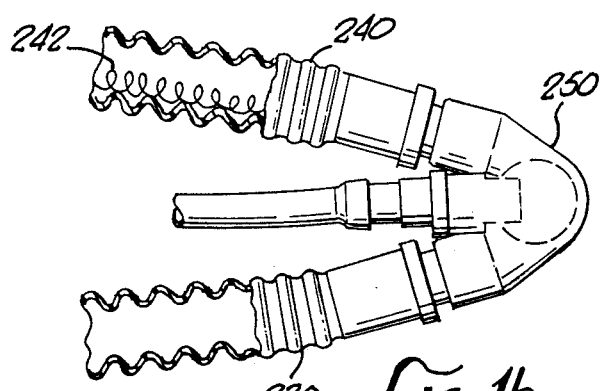
FIG. 1b is a cross section of a prior art parallel, dual tubing breathing circuit.

Unlike the corrugated tubing member shown in the prior art of FIGS. 1a and 1b, the inner surface of the expiratory line 32 is smooth achieving low expiratory flow resistance. High flexibility is achieved by the unique combination of the thin walled expiratory tube 32 and the spiral cord 34.

Figure 6:
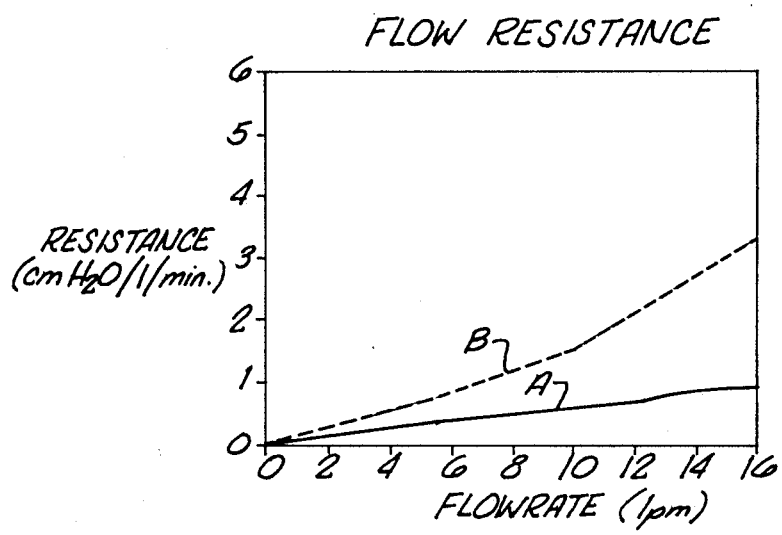
FIG. 6 is a graph comparing the flow resistances of the present invention and the prior art.

FIG. 6 is a graph comparing the flow resistance in the expiratory tubes between the present invention (solid line—A) as compared to a corrugated tubing (dotted line—B) of the prior art (such as in FIG. 1a). The graph shows that at a standard flow rate of about 10 liters per minute (1 pm), the flow resistance of the prior art corrugated tubing B is approximately twice the flow resistance of the present invention A.

In addition to the improved flow resistance, the smooth inner surface of the expiratory tube 3 reduces formation of condensation or "rain out" along its inner surface. The smooth surface eliminates places where condensation may collect and potentially form slugs of water which could potentially cause equipment problems, or if the water flowed back toward the patient connector 50 could create problems for the patient itself. The smooth inner surface of the expiratory line 32 of the present invention provides no pockets in which condensed water may collect.

The formation of condensation pockets of the prior art device also provides a liquid surface which enhances cooling and further condensation. The irregular inner surface of the prior art corrugated tubing not only has a greater surface area for heat transfer and liquid collection but also increases flow turbulence which in and of itself enhances heat transfer thereby further increasing condensation. The smooth inner surface of expiratory tube 32 reduces such heat transfer, lessens turbulence and minimizes rain out.

The present invention also recognizes that compliance, the amount of expansion of the tubes during a breathing cycle, is an important design consideration. The basic process will now be described. The pressure and flow rate through the inspiratory tube 40 remains substantially the same throughout the breathing cycle. To respirate the patient, a valve at the ventilator 5 is opened during exhalation allowing the patient to expel air into the expiratory tube 32 and back to the ventilator 5. Closing the valve at the ventilator 5 prevents air from exiting through the expiratory tube 32 and prompts inhalation as the flow of air from the humidifier 10 increases pressure at the patient connector 50. This intermittent increase in pressure, the peak pressure, exerts expansion forces on the coaxial tube 30 and particularly the expiratory tube 32. During the inhalation portion of the breathing cycle, a desired peak pressure must be reached at the patient's lungs to deliver a desired volume of air within the inhalation period of time. The more the expiratory tube 32 expands, the more air must be injected during the inhalation period to achieve the peak pressure so the desired volume of air is delivered to the patient's lungs. Therefore a lower compliance is desirable.

Tubing with lower compliance requires a lower flow rate to achieve the desired peak pressure. Since the flow rate remains constant throughout the inspiratory and expiratory phases, tubing with lower compliance has a lower flow rate during the expiratory phase. This lower flow rate desirably results in a lower back pressure against which the patient must exhale. Consequently the superior low compliance of the present invention reduces back pressure.

Figure 7:
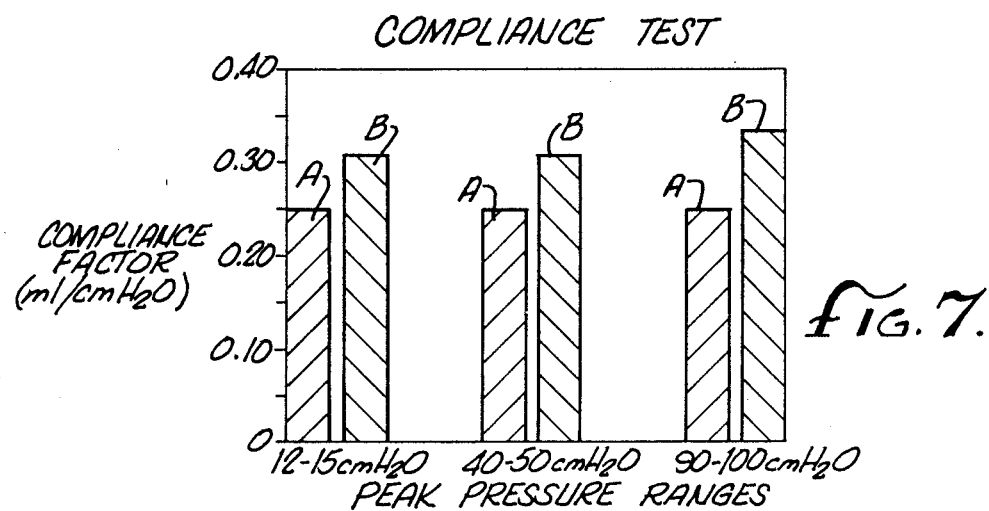
FIG. 7 is a graph comparing the compliance factors of the present invention and the prior art.

While the coaxial tube 30 of the present invention is flexible, it is also desirably less compliant than the corrugated version of the prior art. Structurally comparing the corrugated structure such as tubing 10 of the prior art in FIG. 1a to the tubing 30 of the present invention indicates that the corrugated tubing of the prior art will more readily expand both axially and radially. The graph of FIG. 7 compares the compliance between the standard corrugated coaxial design (B) such as the tubing 110 as compared to the present invention (A). The compliance factor B of the prior art corrugated tubing is 15% to 40% higher than the compliance A of the present invention depending on the peak pressure range. The present invention achieves this superior compliance in part because the design of the flexible cord 34 around the exterior tube 32 and in part by avoiding the greater expansion flexibility inherent in a corrugated tubing design.

The coaxial design of the present invention has several particular advantages over the parallel line design of the prior art device. As shown in FIG. 1b, the prior art has an inspiratory tubing 240 separate from the expiratory tubing 230. The inspiratory tubing 240 has a separate heating line 242 for controlling temperature within the tubing 240, but the external walls of the inspiratory tubing 240 are subjected to ambient temperature. Heat transfer occurs between the warm air inside the tube 240 and the cooler ambient outside air producing condensation along the inner surface of the inspiratory tubing 240.

The coaxial configuration of the present invention has several means for reducing heat transfer (and thereby reducing rain out). First, referring to FIG. 4, the inspiratory tubing 40 is inside the expiratory tubing 32 and thereby insulated from the cooler ambient air outside of the expiratory tubing 32. Second, the heating wire 42 warms both the air in the expiratory tube 32 and the air in the inspiratory tube 40, so the difference in temperature between the air within the two tubes is practically zero. Third, the inner wall of the inspiratory tubing 40 is smooth. The advantages of a smooth inner wall have already been described above with respect to the expiratory tubing 32. Rain out within the inspiratory line 40 is therefore substantially reduced by these and other factors.

Another problem with the parallel tubing of the prior art of FIG. 1b relates to positioning of the patient connector 250. The expiratory line 230 next to the patient is generally oriented downward to avoid allowing condensation collecting within the line to flow back to the patient. The patient connector of the parallel line breathing circuit cannot be rotated to accommodate different patient positions. The concentric design of the coaxial tubing 30 of the present invention has the inspiratory line 40 on the inside and the expiratory line 32 on the outside. The orientation of the inspiratory line 40 relative to the expiratory line 32 remains the same regardless of the position of the patient. Any liquid which happens to collect in the expiratory tubing 32 gravitates to the bottom of the tubing 32 and smoothly moves away from the patient. Therefore the uniquely designed swivel patient connector 50 having a connector ring 52 to which the inner tube 40 and outer tube 32 are attached facilitates patient and device positioning and minimizes torque.

Thus an improved breathing circuit has been shown and described. Though certain advantages and modifications have been described, many more applications and modifications will become apparent to those skilled in the art from the descriptions herein. The invention therefore is to be limited only in the spirit of the claims that follow.

I claim:

1. A breathing circuit comprising:
   a first flexible tube with connection means at each end and
   a second flexible tube inside said first flexible tube and generally coaxial therewith and attached to said connection means at each end, said first and second flexible tubes providing two passageways between said connection means, said first flexible tube having means for effecting low compliance both axially and radially including (a) a spiral cord continuously attached along its length and integral with its outer surface and (b) a non-corrugated tube wall, said first flexible tube having a thin wall relative to the thickness of said second flexible tube and a smooth inner surface along its length.

2. The breathing circuit of claim 1 further comprising a heating wire wound about said second flexible tube.

3. The breathing circuit of claim 1 wherein said connection means comprises a first connector at one end of said flexible tubes for connecting to a breathing apparatus and a second connector at the opposite end for connecting to a patient.

4. The breathing circuit of claim 3 wherein said second connector includes a swivel adapter to facilitate orientation to the patient's position.

5. The breathing circuit of claim 4 wherein said swivel adapter comprises a connector ring to which said first flexible tube and second flexible tubes are attached and a patient connector rotatably connected to said connector ring.

6. The breathing circuit of claim 1 wherein said first flexible tube has a wall thickness about half that of said second flexible tube.

7. A breathing circuit comprising (1) an expiratory tube having a smooth inner surface along its length and means for effecting low compliance both axially and radially including (a) a non-corrugated flexible wall and (b) a plurality of stiffening rings continuously attached to and around its outer surface, said stiffening rings being connected by a connecting means between adjacent stiffening rings and (2) an inspiratory tube inside and generally coaxial with said expiratory tube, wherein said expiratory tube has a thin wall thickness relative to the wall thickness of the inspiratory tube.

8. The breathing circuit of claim 7 wherein said stiffening rings are formed in a continuous helix about the outer surface of said expiratory tube.

9. The breathing circuit of claim 7 wherein said stiffening rings are parallel to one another and consecutively spaced along the length of said expiratory tube.

10. The breathing circuit of claim 7 wherein said stiffening rings are integrally formed with said expiratory tube.

11. The breathing circuit of claim 7 further comprising a heating element for heating gas within said inspiratory tube.

12. The breathing circuit of claim 11 wherein said heating element comprises a heating wire wrapped around said inspiratory tube.

13. A breathing circuit comprising:
   a first flexible tube with connection means at each end;
   a second flexible tube inside said first flexible tube and generally coaxial therewith and attached to said connection means at each end, said first and second flexible tubes providing two passageways between said connection means, said first flexible tube having means for effecting low compliance both axially and radially including (a) a spiral cord continuously attached along its length and integral with its outer surface and (b) a non-corrugated tube wall, said first flexible tube having a thin wall relative to said second flexible tube and a smooth inner surface along its length; and
   a heating means for heating gas within said breathing circuit disposed between said first flexible tube and said second flexible tube.

14. A breathing apparatus comprising:
   a source of gas;
   a humidifier having an outlet connection, the humidifier adapted to be connected to the source of gas;
   a breathing circuit connected to the humidifier outlet connection by an air supply connector, the breathing circuit including: a coaxial tubing set having an inner tubing within an outer tubing, the inner tubing providing inspiratory air passage from the humidifier to a patient with the volume between the inner tubing and the outer tubing providing expiratory air passage from the patient, the outer tubing having with a smooth inner surface along its length and means for effecting low compliance both axially and radially including (a) a non-corrugated flexible wall and (b) a plurality of stiffening rings continuously attached to and around its outer surface, said stiffening rings being connected by a connecting means between adjacent stiffening rings, wherein said outer tubing has a thin wall thickness relative to the wall thickness of the inner tubing;
   a return air line connection between the air supply connector and a return connection on the source of gas; and
   a heating wire disposed between the inner tubing and the outer tubing for controlling gas temperature within the coaxial tubing set.

15. The breathing circuit of claim 14 wherein said source of gas comprises a ventilator.

16. A breathing circuit comprising:
   a coaxial tubing set having an inner tubing with an outer tubing, the inner tubing providing inspiratory air passage from a humidifier to a patient with the volume between the inner tubing and the outer tubing providing expiratory air passage from the patient;
   a heating means disposed between the inner tubing and the outer tubing for controlling gas temperature within the coaxial tubing set,
   wherein the outer tubing includes a smooth inner surface along its length and means for effecting low compliance both axially and radially including (a) a non-corrugated flexible wall and (b) a plurality of stiffening rings continuously attached to and around its outer surface, said stiffening rings being connected by a connecting means between adjacent stiffening rings, wherein said outer tubing has a thin wall thickness relative to the wall thickness of the inner tubing.

* * * * *